(12) United States Patent
Arai (10) Patent No.: US 7,942,819 B2
(45) Date of Patent: May 17, 2011

(54) ULTRASONIC BONE EVALUATION APPARATUS

(75) Inventor: Tatsuo Arai, Nishinomiya (JP)

(73) Assignee: Furuno Electric Company, Limited, Hyogo-ken (JP)

( * ) Notice: Subject to any disclaimer, the term of this patent is extended or adjusted under 35 U.S.C. 154(b) by 1320 days.

(21) Appl. No.: 11/375,074

(22) Filed: Mar. 15, 2006

(65) Prior Publication Data

US 2006/0241439 A1 Oct. 26, 2006

(30) Foreign Application Priority Data

Mar. 17, 2005 (JP) ................................. 2005-076255

(51) Int. Cl.
*A61B 8/00* (2006.01)
(52) U.S. Cl. ....................................... 600/437; 600/438
(58) Field of Classification Search .......... 600/407–480; 702/131, 132; 128/474; 374/117, 170
See application file for complete search history.

(56) References Cited

U.S. PATENT DOCUMENTS

| | | | | |
|---|---|---|---|---|
| 4,232,682 | A * | 11/1980 | Veth | 600/484 |
| 5,944,665 | A | 8/1999 | Iino et al. | |
| 6,015,383 | A | 1/2000 | Buhler et al. | |
| 6,128,523 | A * | 10/2000 | Bechtold et al. | 600/411 |
| 6,352,512 | B1 * | 3/2002 | Wilson et al. | 600/449 |
| 2002/0055693 | A1 * | 5/2002 | Thompson et al. | 601/2 |
| 2003/0176789 | A1 * | 9/2003 | Kaplan | 600/438 |
| 2004/0122494 | A1 * | 6/2004 | Eggers et al. | 607/103 |
| 2004/0243003 | A1 * | 12/2004 | Pasternak et al. | 600/449 |
| 2005/0096547 | A1 * | 5/2005 | Wendelken et al. | 600/459 |

FOREIGN PATENT DOCUMENTS

| | | |
|---|---|---|
| CN | 1584523 A | 2/2005 |
| CN | 100488458 C | 5/2009 |
| EP | 0747011 A2 | 12/1996 |
| EP | 1 038 501 A1 | 3/2000 |
| EP | 1557126 A1 | 7/2005 |

(Continued)

OTHER PUBLICATIONS

Nasoni, Richard L.; "Temperature corrected speed of sound for use in soft tissue imaging;" 1981 Am. Assoc. Phys. Med.; Med. Phys. 8(4), Jul./Aug. 1981, 0094-2405/81/040513-04$01.20; pp. 513-515.*

*Primary Examiner* — Tse Chen
*Assistant Examiner* — Vani Gupta
(74) *Attorney, Agent, or Firm* — Antonelli, Terry, Stout & Kraus, LLP.

(57) ABSTRACT

An ultrasonic bone evaluation apparatus includes stationary and movable standoffs fitted with respective ultrasonic transducers for transmitting and receiving ultrasound, a moving mechanism for moving the movable standoff, an encoder, a controller, and an inner temperature sensor for determining the temperature of an inner tissue of a body part. The moving mechanism moves the movable standoff toward the stationary standoff to sandwich the body part therebetween. The encoder measures the distance between the two transducers whereas the controller determines the time required for the ultrasound to travel between the transducers when the body part is sandwiched between the standoffs. The controller calculates the speed of sound propagating through the body part from distance and time measurement values, corrects the speed of sound through the body part based on the temperature of the body part measured by the inner temperature sensor, and evaluates the bone of the body part based on the corrected speed of sound.

5 Claims, 4 Drawing Sheets

FOREIGN PATENT DOCUMENTS

| | | | |
|---|---|---|---|
| GB | 2321704 A | * | 8/1998 |
| JP | 06-197895 | | 7/1994 |
| JP | 06197895 A | | 7/1994 |
| JP | 06327669 A | * | 11/1994 |
| JP | 9-218033 | | 8/1997 |
| JP | 2840040 | | 10/1998 |
| JP | 2000-325349 | | 11/2000 |
| JP | 2005-098982 | | 4/2005 |

* cited by examiner

ULTRASONIC BONE EVALUATION APPARATUS

BACKGROUND OF THE INVENTION

1. Field of the Invention

The present invention relates to an ultrasonic bone evaluation apparatus for evaluating bone of a living organism by using ultrasound.

2. Description of the Related Art

Osteoporosis is of great concern in recent years that provokes an increasing need for evaluation of bone. While a mainstream method conventionally used for bone assessment is radiological diagnosis using X rays, ultrasonographic bone assessment is becoming increasingly popular today. Compared to the conventional X-ray method, ultrasonography is advantageous in that an ultrasonic diagnostic apparatus can be constructed more compactly and relieve stress on examinees requiring less measurement time and no exposure to X rays. An index often used for bone assessment is the speed of sound (SOS) at which ultrasound waves propagate through bone tissue.

Japanese Patent No. 2840040 discloses one conventional approach to measuring the speed of sound propagating through a body part of an examinee with high accuracy. This approach involves the use of a temperature sensor for measuring the temperature of an acoustic matching medium filled within a transducer cover. The speed of sound passing through the acoustic matching medium is corrected based on the temperature thereof measured by the temperature sensor to obtain an accurate measurement of the ultrasound speed through the body part being examined.

Another previous approach is found in Japanese Patent Application Publication No. 1994-197895. This approach makes use of a vessel containing acoustic matching liquid in which a body part to be examined is placed and a temperature sensor for measuring the temperature of the body part. The temperature of the acoustic matching liquid is adjusted based on the measured temperature of the body part, and measurement of ultrasonic wave propagation property (speed of sound) is commenced when the temperature of the acoustic matching liquid and the temperature of the body part reach equilibrium with each other. According to the Publication, this approach makes it possible to perform ultrasonographic measurement with good repeatability in a stable fashion.

The calcaneus is most often used in the evaluation of bone architecture by an ultrasonographic measuring apparatus. Generally, the speed of ultrasound propagating through the calcaneus measured by the apparatus is affected by the temperature of the heel which causes considerable variations in ultrasound speed measurements. Such variations in ultrasound speed measurements are particularly significant during winter when the temperature of the heel is low.

Conventionally, an examinee is forced to wait in a well-heated waiting room for a long time (nearly one hour) before measurement until the heel warms. Although measurement errors can be almost avoided in this way, this conventional approach is not quite efficient because the examinee must spend a long waiting time, resulting in a reduction in measurement efficiency.

The aforementioned approach of Japanese Patent No. 2840040 is to simply correct the speed of sound passing through the acoustic matching medium by using the temperature of the acoustic matching medium measured by the temperature sensor, so that variations in the ultrasound speed through the heel due to changes in the temperature of the heel can not be corrected by this approach.

According to the aforementioned approach of Japanese Patent Application Publication No. 1994-197895, on the other hand, measurement can be started only after the temperature of the body part to be examined has become equal to the temperature of the acoustic matching liquid. Thus, this approach requires a long measurement time and results in poor measurement efficiency. In addition, the examinee must place the body part to be examined (typically, one of the feet) in the acoustic matching liquid filled in the vessel with the approach of this Publication. This is not quite comfortable for the examinee and makes it necessary to take measures to maintain properly controlled hygienic conditions.

There exists another conventional approach to reducing variations in the ultrasound speed through the heel due to changes in the temperature of the heel. This approach is to combine the aforementioned measurement of the speed of sound (SOS) and a measurement of frequency-dependent broadband ultrasonic attenuation (BUA) of the body part being measured. This approach requires complex calculation and imposes heavy load on a processing device which performs mathematical operation for bone assessment.

SUMMARY OF THE INVENTION

In view of the foregoing, it is an object of the invention to provide an ultrasonic bone evaluation apparatus for evaluating bone of a living organism by using ultrasound with high measurement accuracy.

According to one aspect of the present invention, there is provided an ultrasonic bone evaluation apparatus having a pair of ultrasonic transducers on both sides of a body part for transmitting and receiving ultrasounds by the ultrasonic transducers to measure the speed of sound propagating through the body part and for evaluating bone of the body part based on the speed of sound. The ultrasonic bone evaluation apparatus comprises a temperature measuring unit for measuring or estimating the temperature of the body part, and means for compensating for variations of the speed of sound in the body part due to temperature based on a temperature measured by the temperature measuring unit.

According to another aspect of the invention, there is provided an apparatus for adjusting a measured velocity of sound propagated through a body part which comprises a temperature detector, including a sensor for measuring a temperature of the body part, and configured to output an inner temperature of the body part corresponding to the measured temperature, and a processor configured to adjust the measured velocity of the sound propagated through the body part based on the output inner temperature.

According to another aspect of the invention, there is provided an ultrasonic bone evaluation apparatus for evaluating bone of a body part based on the speed of sound propagating therethrough. The ultrasonic bone evaluation apparatus includes a pair of standoffs having contact surfaces and fitted with respective ultrasonic transducers for transmitting and receiving ultrasound, with the standoffs being disposed face to face with each other, a moving mechanism for moving at least one of the two standoffs so that the body part is in contact with the contact surfaces of the two standoffs, a distance measuring device for measuring the distance between the contact surfaces of the two standoffs, a time measuring device for measuring the time required for the ultrasound to travel in the body part, and a temperature measuring device for measuring the temperature of the body part sandwiched between the two standoffs. The speed of sound propagating through the body part is corrected based on the temperature thereof measured by the temperature measuring device. The ultrasonic bone evaluation apparatus evaluates the bone of the body part by using the speed of sound thus corrected.

The ultrasonic bone evaluation apparatus thus structured can evaluate the bone of the body part being examined with high accuracy and with minimum deterioration of the accuracy potentially caused by changes in the temperature of the body part. The bone can be evaluated with high accuracy and reduced variations in evaluation results regardless of changes in the temperature of the body part.

Preferably, the temperature measuring device measures the temperature of the body part several times at properly determined time intervals and estimates the temperature of the body part which will be reached under equilibrium conditions from a plurality of temperature measurement values thus obtained.

The ultrasonic bone evaluation apparatus thus structured is advantageous in that the time required for measuring the temperature of the body part can be substantially reduced.

Preferably, the ultrasonic bone evaluation apparatus further includes a support mechanism (foot support) for supporting the body part to be examined, and the temperature measuring device is disposed in the support mechanism.

The ultrasonic bone evaluation apparatus thus structured can measure the temperature of the body part if only an examinee places the body part to be examined on the support mechanism without causing stress on the examinee.

Still preferably, the temperature measuring device is a temperature sensor for measuring a temperature in the body part.

The ultrasonic bone evaluation apparatus thus structured can measure or estimate the temperature of the body part with high accuracy and little influence of outdoor temperature. Additionally, the ultrasonic bone evaluation apparatus can measure the temperature of the body part at a deeper location thereof in a noninvasive manner. Thus, as compared to conventional bone evaluation apparatuses, the ultrasonic bone evaluation apparatus of the invention can evaluate the bone of the body part with much reduced stress on the examinee.

According to further aspect of the invention, there is provided an ultrasonic bone evaluation apparatus for evaluating bone of a body part by use of ultrasound which includes a pair of ultrasonic transducers for transmitting and receiving the ultrasound, with the ultrasonic transducers being disposed on both sides of the body part and having contact surfaces provided at forward ends of the individual ultrasonic transducers. In this ultrasonic bone evaluation apparatus, at least one of the contact surfaces is made movable toward and away from the body part so that the contact surfaces are placed in direct contact with the body part. The ultrasonic bone evaluation apparatus measures or estimates the temperature of the body part and the speed of sound propagating therethrough, corrects the speed of sound through the body part based on the measured temperature thereof, and evaluates the bone of the body part based on the corrected speed of sound propagating through the body part.

The ultrasonic bone evaluation apparatus thus structured can evaluate the bone of the body part being examined with high accuracy and with minimum deterioration of the accuracy potentially caused by changes in the temperature of the body part.

According to further aspect of the invention, there is provided a method for adjusting a measured velocity of sound propagated through a body part which comprises measuring a temperature of the body part, adjusting the measured velocity of the sound propagated through the body part based on an inner temperature of the body part corresponding to the measured temperature.

These and other objects, features and advantages of the invention will become more apparent upon reading the following detailed description along with the accompanying drawings.

DETAILED DESCRIPTION OF THE PREFERRED EMBODIMENT OF THE INVENTION

Figure 1:
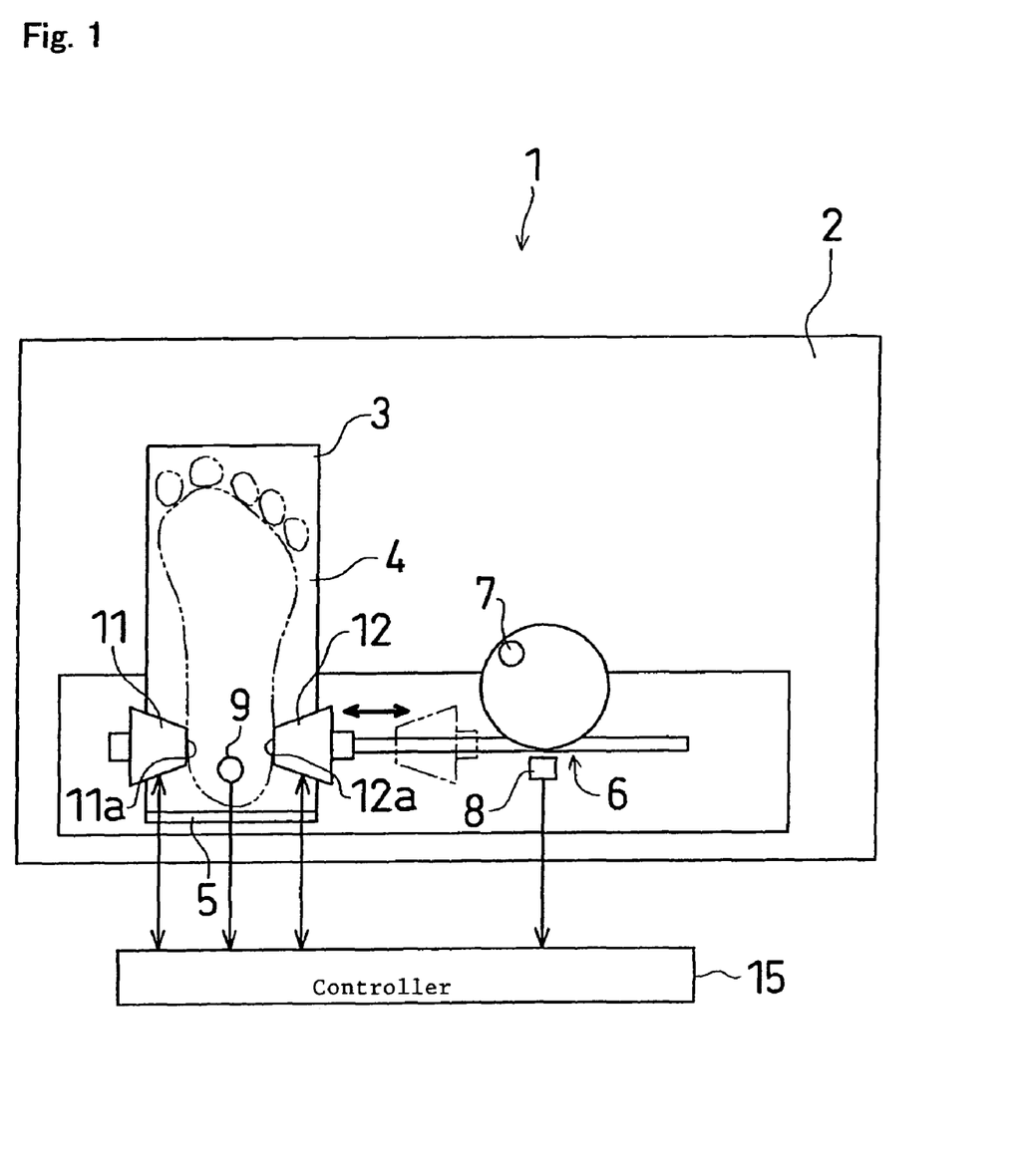
FIG. 1 is a plan view schematically showing the configuration of a bone evaluation apparatus according to a preferred embodiment of the invention.
Figure 2:
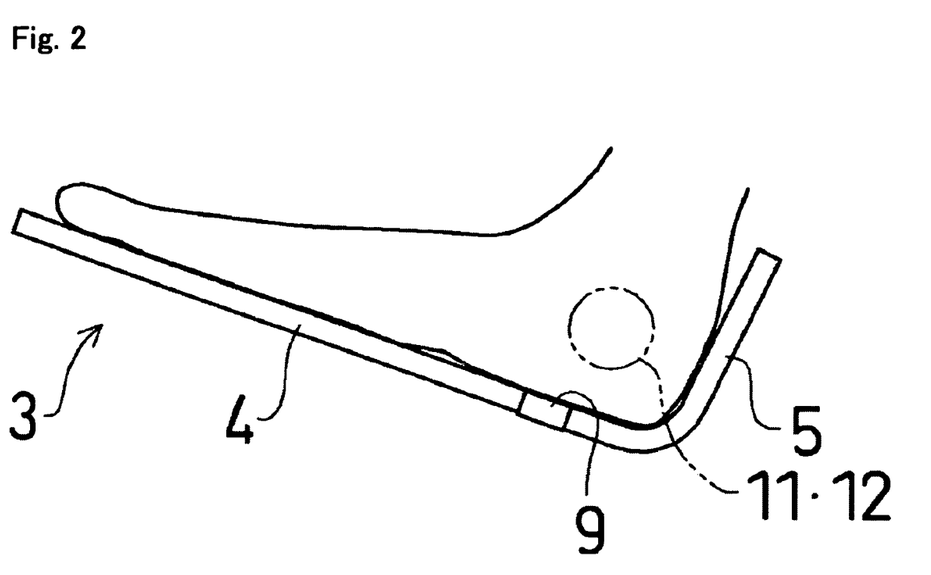
FIG. 2 is a fragmentary side view showing how an examinee places one of the feet on a foot support of the bone evaluation apparatus.

The invention will be explained hereinafter in detail with reference to a preferred embodiment thereof which is illustrated in the accompanying drawings, of which FIG. 1 is a plan view schematically showing the configuration of a bone evaluation apparatus 1 according to the embodiment of the invention, and FIG. 2 is a fragmentary side view showing how an examinee places one of the feet on a foot support 3 of the bone evaluation apparatus 1.

The bone evaluation apparatus 1, which is a typical example of an ultrasonic bone evaluation apparatus, is provided with the aforementioned foot support 3 disposed at the top of a main unit 2 so that the examinee can place the foot on the foot support 3 as illustrated by alternate long and two short dashed lines in FIG. 1.

Referring to FIG. 2, the foot support 3 includes a slightly inclined bottom portion 4 on which the foot can be positioned with the toe directed obliquely upward and a heel supporting portion 5 raised from a rear end of the bottom portion 4 to enable the examinee to hold the foot in position with the heel rested against the heel supporting portion 5.

The main unit 2 of the bone evaluation apparatus 1 includes a stationary standoff 11 and a movable standoff 12 which are mounted such that the heel of the examinee placed on the foot support 3 can be located between the stationary and movable standoffs 11, 12. The two standoffs 11, 12 are fitted with respective ultrasonic transducers (not shown) which are directed face to face with each other so that each of the transducers can transmit ultrasound waves and receive ultrasound waves which pass through or are reflected by the heel or by the surfaces (boundaries) of the standoffs. At foremost ends of the standoffs 11, 12 there are provided contact surfaces 11a, 12a, respectively, which go into direct contact with the heel (probing site), the contact surfaces 11a, 12a facing each other.

The movable standoff 12 having the contact surface 12a is supported by a moving mechanism which is made up of a rack-and-pinion mechanism 6 in this embodiment. The movable standoff 12 can be moved toward or away from the stationary standoff 11, or the probing site, by turning a knob handle 7. In the bone evaluation apparatus 1 thus structured, an operator can move the movable standoff 12 apart from the stationary standoff 11 when the examinee places the foot on the foot support 3 and upon completion of an examination.

When carrying out the examination, the operator moves the movable standoff 12 toward the stationary standoff 11 such that the two standoffs 11, 12 hold the heel from both sides in close contact therewith.

The aforementioned rack-and-pinion mechanism 6 is equipped with a torque limiter (not shown) which prevents the movable standoff 12 from pushing against the heel with an excessive force even when the operator forcibly turns the knob handle 7.

The rack-and-pinion mechanism 6 for moving the movable standoff 12 is provided with an encoder 8 which serves as a distance measuring device for determining the distance from the stationary standoff 11 to the movable standoff 12, especially when the heel is held between the stationary and movable standoffs 11, 12. This arrangement makes it possible to calculate the distance between the stationary and movable standoffs 11, 12 and, thus, the width of the heel of the examinee.

When carrying out an examination, the bone evaluation apparatus 1 transmits an ultrasound signal at a specific frequency from the transducers attached to both standoffs 11, 12, measures the time elapsed between transmission and reception of the ultrasound signal (or the time required for the ultrasound signal to travel between the two transducers), and calculates the speed of sound passing through the heel from the time thus measured and the width of the heel derived from a measurement value obtained by the encoder 8. Then, the bone evaluation apparatus 1 calculates bone salt content and outputs calculation results representative of the results of bone assessment on a display screen (not shown), for example.

The aforementioned measurement and calculation of the ultrasound propagation time through the heel are performed under the control of a controller 15 which stores a microcomputer algorithm of the prior art, the controller 15 including a central processing unit (CPU), a read-only memory (ROM) and a random access memory (RAM) which are not illustrated. The controller 15 is electrically connected to the encoder 8 and the ultrasonic transducers fitted to both standoffs 11, 12.

The bone evaluation apparatus 1 further includes an inner temperature sensor 9 disposed in the bottom portion 4 of the foot support 3 for measuring the temperature of the probing part at a deep location thereof. The ultrasound propagation time through the heel can be determined more exactly with the temperature measured at a deeper location in the heel than with surface temperature thereof. For example, the core temperature monitor Model CM-210 manufactured by Terumo Corporation, Japan usable in a later-described experiment is designed to measure bone temperatures at a deep location thereof based on the fact that the surface temperature becomes equal to the temperature at a deeper location if the surface of the probing site is properly insulated. The bone evaluation apparatus 1 of the embodiment determines the bone temperature of the probing part at a deep location thereof from measurement results obtained by such a temperature measuring device for measuring a temperature at a depth in the body or through estimation from the measurement results. Specifically, the controller 15 obtains the temperature of the heel of the examinee from the inner temperature sensor 9 which is electrically connected to the controller 15.

More specifically, for calculating the speed of sound passing through the heel, the controller 15 of the bone evaluation apparatus 1 obtains the temperature of the heel of the examinee measured by the inner temperature sensor 9 under thermal equilibrium conditions and corrects the speed of sound by using a previously known correlation between the propagating speed of sound and temperature characteristics. This approach makes it possible to reduce variations in measurement values of the ultrasound speed due to its temperature characteristics.

The correlation between the speed of sound propagating through the heel and the temperature thereof is determined from a clinical experiment performed by a procedure described below.

The experiment involves measuring the temperature of the heel and the speed of sound passing therethrough twice and examining changes in measurement values. It is preferable that two pairs of heel temperature and ultrasound speed measurements be taken under different ambient temperature conditions. It is possible to determine the correlation between heel temperature and ultrasound speed therethrough with high accuracy from a comparison of measurements obtained in winter and summer, or in the morning and afternoon of a winter day, for example.

The inventors carried out experiments to examine changes in measurement values of heel temperature and ultrasound speed therethrough taken in the morning and afternoon in January and February on twenty-one female subjects ranging from 22 to 56 years of age. The morning measurements were taken between 9 and 11 a.m. The outdoor temperature in the morning was 6° C. to 12° C. on days when the experiments were conducted. The subjects entered a room heated to 23° C. to 26° C. at about 9 o'clock on a day in January or February. The afternoon measurements were taken between 2 and 4 p.m. on the same day as the morning measurements were taken. The subjects stayed in the room throughout the afternoon measurements and the afternoon measurements.

While the inventors carried out the experiments using the same configuration as shown in FIG. 1 for determining the speed of sound passing through the heel, commercially available instruments may be used for measuring the speed of sound and the heel temperature at a deep location of the body for the purpose of determining the correlation therebetween.

Figure 3:
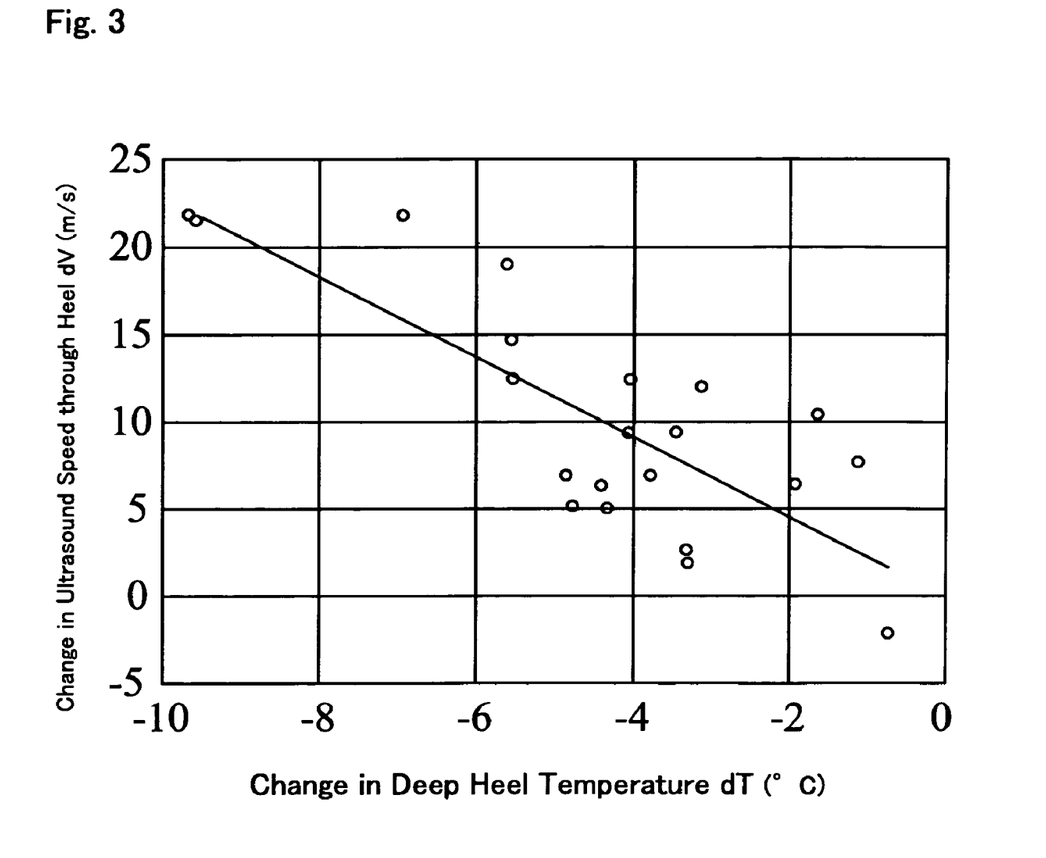
FIG. 3 is a graphical representation of experimental results showing a relationship between changes in the temperature of the heel at a deep location thereof and changes in ultrasound speed through the heel.

FIG. 3 is a graphical representation of experimental results showing a relationship between deep temperature change dT in the heel and sound speed change dV through the heel, where dT=(heel temperature measured in the morning)−(heel temperature measured in the afternoon) and dV=(sound speed measured in the morning)−(sound speed measured in the afternoon). According to the experimental results, the speed of sound propagating through the heel ranges from 1,491 m/s to 1,562 m/s and averages 1,511 m/s.

The experimental results shown in FIG. 3 indicate that there is a tendency for the speed of sound through the heel to decrease with an increase in the heel temperature. From a linear approximation of the measurements shown by small circles in FIG. 3 by the least squares method, the inventors have found that there is a relationship expressed by dV=−2.27 dT between the sound speed change dV and the deep temperature change dT in the heel. As an example, the bone evaluation apparatus 1 may use this correlation function to correct the measured speed of sound propagating through the heel.

A correlation coefficient (correction coefficient) to be used for correcting the speed of sound propagating through the heel can be obtained not only from the results of the clinical experiment as mentioned above but also from a study of physical bone properties. For example, the correction coefficient can be determined from actually measured temperature coefficients of such soft bones as spongy bone constituting most part of the calcaneus and subcutaneous fat. The temperature coefficient of the speed of sound propagating through the heel is nearly proportional to the temperature coefficient of the calcaneus on average. Specifically, the temperature coefficient of the speed of sound propagating through the heel is estimated at approximately −2.5 m/s/° C., which corresponds well with the aforementioned clinical measurement result (dV=−2.27 dT).

The correction coefficient used in the bone evaluation apparatus 1 of the embodiment is obtained essentially from actual measurements as discussed above. Thus, the correction coefficient may be updated to a more accurate value obtained through an accumulation of clinical data and analysis data.

Now, a specific example of ultrasound speed measurement performed by using the correction coefficient is described. First, the operator sets the aforementioned correction coefficient, that is, the temperature coefficient representing the ratio of a change in the speed of sound to a change in the heel temperature, in the bone evaluation apparatus 1. Specifically, the operator sets the value −2.5 m/s/° C. obtained from the clinical experiment in the bone evaluation apparatus 1 so that this value is stored in the controller 15. The operator also sets a "standard temperature" of the heel to be examined at 30° C., for example, in the bone evaluation apparatus 1 so that this value is stored in the controller 15.

Next, the bone evaluation apparatus 1 measures the deep tissue temperature of the heel sandwiched between the two standoffs 11, 12 by means of the inner temperature sensor 9 as well as the speed of sound V propagating through the heel. The controller 15 compares the temperature of the heel measured by the inner temperature sensor 9 with the aforementioned standard temperature. If the measured heel temperature is equal to or higher than the standard temperature, the controller 15 regards current measurement conditions as being normal and does not make any correction to the measured sound speed V.

If the measured heel temperature is lower than the standard temperature, on the other hand, the controller 15 calculates the difference between the measured heel temperature and the standard temperature and obtains a temperature correction value dV by multiplying the measured heel temperature by the aforementioned correction coefficient. The controller 15 calculates a sound speed V corrected by the temperature correction value dV and determines the speed of sound propagating through the heel from the sound speed V thus obtained. The bone evaluation apparatus 1 can obtain an exact sound speed measurement value in this way.

As illustrated in the foregoing discussion, the bone evaluation apparatus 1 of the embodiment includes the pair of standoffs 11, 12 which are fitted with the respective ultrasonic transducers directed face to face with each other, the rack-and-pinion mechanism 6 for moving one of the standoffs 11, 12 (the movable standoff 12), the encoder 8 for measuring the distance between the stationary and movable standoffs 11, 12, and the controller 15 for calculating the time required for the ultrasound to propagate through the heel placed between the two standoffs 11, 12. The bone evaluation apparatus 1 is so structured as to move the movable standoff 12 by the rack-and-pinion mechanism 6 to sandwich the heel between the stationary and movable standoffs 11, 12, measure the distance between the two standoffs 11, 12 and the time required for the ultrasound to propagate through the heel, calculate the speed of sound propagating through the heel from the measured distance and propagation time, and evaluate the bone of the heel by using the speed of sound thus determined. The bone evaluation apparatus 1 further includes the inner temperature sensor 9 for measuring or estimating the temperature of the heel sandwiched between the two standoffs 11, 12, whereby the controller 15 corrects the calculated speed of sound propagating through the heel based on the temperature of the heel obtained by the inner temperature sensor 9 and evaluates the bone of the heel by using the corrected speed of sound.

The bone evaluation apparatus 1 thus structured can correct the calculated speed of sound propagating through the heel by measuring the temperature of the heel as thus far discussed. This structure of the present embodiment makes it possible to reduce variations in measurement values of the sound speed through the heel as well as variations in evaluation values of the probing site, such as bone salt content measurements.

The structure of the embodiment may be modified to include provision for giving audible and/or visual warning by means of an on-screen display or a buzzer when the measured heel temperature does not fall within a predefined range, instead of the above-described arrangement for correcting the speed of sound based on the heel temperature. This modified form of the embodiment can also reduce the possibility of producing inaccurate measurements due to a heel temperature higher than or lower than a normal temperature range and thereby improve the accuracy of sound speed measurements.

As the inner temperature sensor 9 is fitted in the foot support 3 in the foregoing embodiment, the bone evaluation apparatus 1 can measure the temperature of the heel if an examinee simply places the foot on the foot support 3. Thus, the bone evaluation apparatus 1 of the embodiment enables the operator to perform measurements for bone assessment with substantially the same amount of labor as with conventionally known bone evaluation apparatuses. Since the bone evaluation apparatus 1 is provided with the inner temperature sensor 9, the bone evaluation apparatus 1 can measure the temperature of the heel at a deeper location thereof with little influence of the outdoor temperature in a noninvasive manner without using a needle, for example. Therefore, compared to the conventional bone evaluation apparatuses, the bone evaluation apparatus 1 of the embodiment can evaluate the bone of the probing site with much reduced stress on the examinee.

Figure 4:
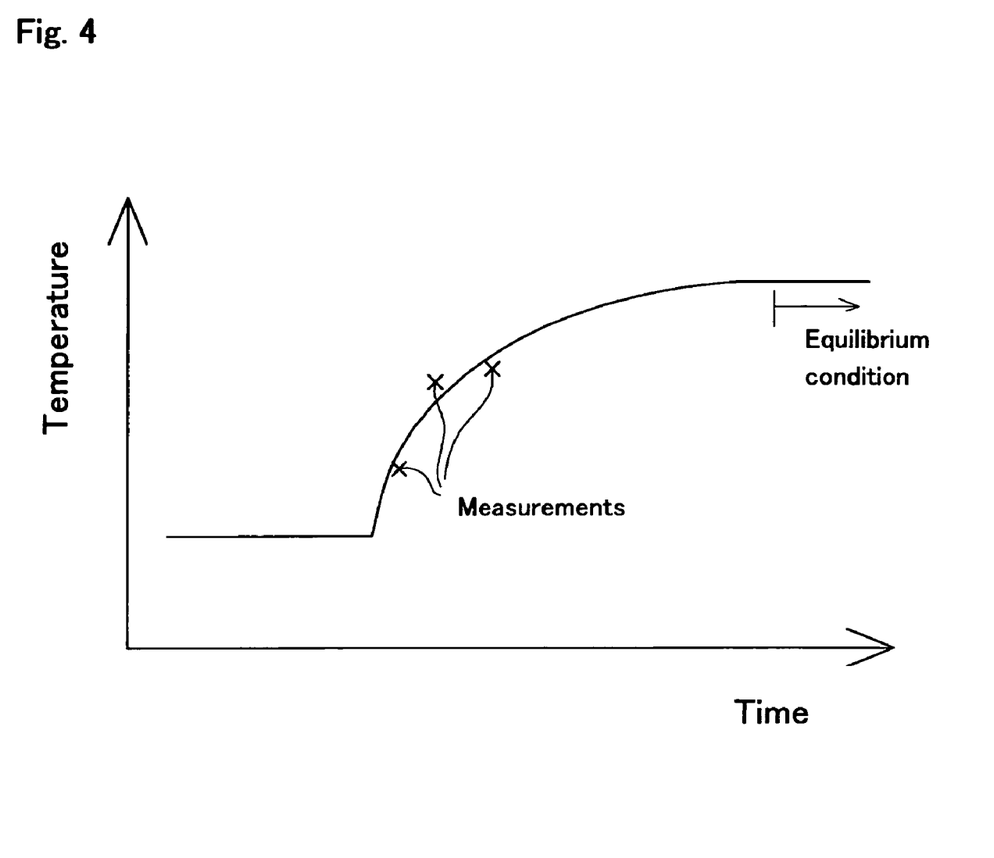
FIG. 4 is a graphical representation of how the temperature of the heel is measured before thermal equilibrium conditions are reached.

While the bone evaluation apparatus 1 of the foregoing embodiment is structured to measure the temperature of the heel under thermal equilibrium conditions by means of the inner temperature sensor 9, the invention is not limited to this structure. For example, the bone evaluation apparatus 1 may be modified to measure the temperature of the heel several times at appropriate time intervals before the heel temperature reaches equilibrium as shown in FIG. 4 and estimate the temperature of the heel which will be reached under equilibrium conditions from a plurality of measurement values thus obtained. This modified form of the embodiment is advantageous in that the time required for measuring the heel temperature and, thus, the time required for determining the speed of sound propagating through the heel can be substantially reduced. The temperature of the heel which will be reached under thermal equilibrium conditions can be estimated by using a generally known formula applicable to estimation of temperature changes which occur in two objects of different temperatures due to heat transfer therebetween when the two objects are brought into mutual contact. A temperature increase curve may be approximated from the plurality of measurement values by using the least squares method, for instance.

While the invention has thus far been described, by way of example, with reference to the preferred embodiment and modifications thereof, the invention is not limited thereto but may be otherwise modified within the scope of the appended claims.

For example, the inner temperature sensor 9 may be used for measuring not only the speed of sound propagating through the heel but also broadband ultrasonic attenuation.

Also, the bone evaluation apparatus 1 may be modified such that both of the two standoffs 11, 12 can be moved to hold the probing site of the examinee in between. Furthermore, the bone evaluation apparatus 1 may be modified such that at least one of the contact surfaces 11a, 12a of the standoffs 11, 12 can be moved without changing the distance between the two ultrasonic transducers.

The probing site of the examinee to be examined by the bone evaluation apparatus 1 is not limited to the heel but the bone evaluation apparatus 1 can be adapted to measure a properly selected body part other than the heel of the examinee. It will be appreciated, however, that the bone evaluation apparatus 1 of the foregoing embodiment configured to measure the heel is particularly preferable in that the apparatus 1 can be constructed compactly, yet providing a capability to easily evaluate the probing site with reduced stress on the examinee.

What is claimed is:

1. An ultrasonic bone evaluation apparatus for evaluating bone of a body part based on the speed of sound propagating therethrough, the ultrasonic bone evaluation apparatus comprising:
    a pair of standoffs having contact surfaces respectively and fitted with respective ultrasonic transducers for transmitting and receiving ultrasound, said standoffs being disposed face to face with each other;
    a moving mechanism for moving at least one of said two standoffs so that the body part is in contact with the contact surfaces of the two standoffs;
    a distance measuring device for measuring the distance between the contact surfaces of the standoffs when the body part is in contact with the contact surfaces of said two standoffs;
    a time measuring device for measuring the time required for the ultrasound to travel in the body part;
    a temperature measuring device for measuring the temperature of the body part sandwiched between said two standoffs; and
    a processor configured to correct the speed of sound propagating through the body part based on the temperature thereof measured by said temperature measuring device and to evaluate the bone of the body part by using the speed of sound thus corrected.

2. The ultrasonic bone evaluation apparatus according to claim 1, wherein said temperature measuring device measures the temperature of the body part a plurality of times at time intervals and estimates the temperature of the body part which will be reached under equilibrium conditions from a plurality of temperature measurement values thus obtained.

3. The ultrasonic bone evaluation apparatus according to claim 1, further comprising:
    a support mechanism for supporting the body part, wherein said temperature measuring device is disposed in said support mechanism.

4. The ultrasonic bone evaluation apparatus according to claim 1, wherein said temperature measuring device is a temperature sensor for measuring a temperature in the body part.

5. An ultrasonic bone evaluation apparatus for evaluating bone of a body part by use of ultrasound, the ultrasonic bone evaluation apparatus comprising:
    a pair of ultrasonic transducers for transmitting and receiving ultrasounds, said ultrasonic transducers being disposed on both sides of the body part and having contact surfaces provided at forward ends of said individual ultrasonic transducers;
    a processor;
    a support mechanism for supporting the body part; and
    a temperature measuring device disposed in said support mechanism;
    wherein at least one of said contact surfaces is made movable toward and away from the body part so that said contact surfaces are placed in contact with the body part; and
    wherein said processor measures the speed of sound propagating through the body part, corrects the speed of sound through the body part based on a temperature thereof measured by the temperature measuring device, and evaluates the bone of the body part based on the corrected speed of sound propagating through the body part.

* * * * *